US010290031B2

(12) United States Patent
Reid (10) Patent No.: US 10,290,031 B2
(45) Date of Patent: May 14, 2019

(54) METHOD AND SYSTEM FOR AUTOMATED RETAIL CHECKOUT USING CONTEXT RECOGNITION

(71) Applicant: Gregorio Reid, Boquete (PA)

(72) Inventor: Gregorio Reid, Boquete (PA)

(*) Notice: Subject to any disclaimer, the term of this patent is extended or adjusted under 35 U.S.C. 154(b) by 751 days.

(21) Appl. No.: 14/322,204

(22) Filed: Jul. 2, 2014

(65) Prior Publication Data

US 2015/0039458 A1    Feb. 5, 2015

Related U.S. Application Data

(60) Provisional application No. 61/857,994, filed on Jul. 24, 2013.

(51) Int. Cl.
| | | |
|---|---|---|
| *G06Q 30/00* | (2012.01) | |
| *G06Q 30/06* | (2012.01) | |
| *A61B 5/117* | (2016.01) | |
| *G06K 9/00* | (2006.01) | |
| *G07G 1/00* | (2006.01) | |
| *G06Q 20/20* | (2012.01) | |
| *G06Q 20/40* | (2012.01) | |
| *A61B 5/1171* | (2016.01) | |
| *A61B 5/11* | (2006.01) | |

(52) U.S. Cl.
CPC ......... *G06Q 30/0601* (2013.01); *A61B 5/117* (2013.01); *G06K 9/00335* (2013.01); *G06K 9/00771* (2013.01); *G06Q 20/206* (2013.01); *G06Q 20/40145* (2013.01); *G07G 1/0036* (2013.01); *A61B 5/112* (2013.01); *A61B 5/1176* (2013.01)

(58) Field of Classification Search
CPC ...................................................... G06Q 30/00
See application file for complete search history.

(56) References Cited

U.S. PATENT DOCUMENTS

| | | | | |
|---|---|---|---|---|
| 6,522,772 B1 * | 2/2003 | Morrison | ............. | G06Q 20/208 235/383 |
| 7,010,501 B1 * | 3/2006 | Roslak | .................. | G06Q 20/20 705/23 |
| 7,394,346 B2 * | 7/2008 | Bodin | ..................... | G06F 3/017 340/10.1 |

(Continued)

OTHER PUBLICATIONS

Zimmerman, Ann, "CheckOut the Future of Shopping Shaving Time Off the Weekly Grocery Run to Keep Consumers in stores and spending", dated May 18, 2011. (Year: 2011).*

(Continued)

*Primary Examiner* — Mark A Fadok
(74) *Attorney, Agent, or Firm* — Kevin H. Fortin (57) ABSTRACT

A gestural checkout system includes a sensor-equipped server programmed with a gestural context application that authenticates a customer's identity upon entry to a retail store. The sensors include cameras. The sensors are identify products and detect gestures of the customer indicating a purchase decisions. Gestures include product pick-up, product movement and product-commit-to-container actions. For bulk items, an Implicit Gestural Scale communicates product identity and volumetric data wirelessly to the implicit gestural checkout. Recognition of shopper locomotion, past a line of demarcation near the exit, automatically authorizes electronic payment.

21 Claims, 6 Drawing Sheets

(56) References Cited

U.S. PATENT DOCUMENTS

| | | | | |
|---|---|---|---|---|
| 7,931,194 B2* | 4/2011 | Keys | G06Q 20/341 | 235/379 |
| 7,957,725 B2* | 6/2011 | Van Erlach | G06Q 30/0207 | 455/41.1 |
| 8,418,919 B1* | 4/2013 | Beyda | G07G 1/0054 | 235/375 |
| 8,531,396 B2* | 9/2013 | Underkoffler | G06F 3/017 | 345/158 |
| 8,758,102 B2* | 6/2014 | Block | G06Q 30/02 | 463/1 |
| 8,843,760 B2* | 9/2014 | Atherton | G06F 21/32 | 713/186 |
| 8,856,034 B2* | 10/2014 | Abraham | G07G 1/14 | 235/383 |
| 8,924,255 B1* | 12/2014 | Koo | G06Q 30/0261 | 705/14.58 |
| 9,367,770 B2* | 6/2016 | Footen | G06K 9/78 | |
| 9,892,438 B1* | 2/2018 | Kundu | G06Q 30/0609 | |
| 2002/0113123 A1* | 8/2002 | Otto | G06K 17/0022 | 235/381 |
| 2003/0020707 A1* | 1/2003 | Kangas | G06F 3/011 | 345/418 |
| 2007/0138260 A1* | 6/2007 | Keys | G06Q 20/341 | 235/380 |
| 2011/0131083 A1* | 6/2011 | Redmann | B60L 11/1816 | 705/13 |
| 2011/0166694 A1* | 7/2011 | Griffits | G07F 9/02 | 700/215 |
| 2011/0183732 A1* | 7/2011 | Block | G06Q 30/02 | 463/1 |
| 2012/0284209 A1* | 11/2012 | Duffy | G07B 15/02 | 705/418 |
| 2013/0055354 A1* | 2/2013 | Weinberg | G06Q 30/0631 | 726/4 |
| 2013/0076898 A1* | 3/2013 | Philippe | H04N 7/18 | 348/143 |
| 2013/0103486 A1* | 4/2013 | Hess | G06Q 30/02 | 705/14.38 |
| 2013/0103519 A1* | 4/2013 | Kountotsis | G07G 1/0036 | 705/23 |
| 2013/0126611 A1* | 5/2013 | Kangas | G06K 7/10178 | 235/385 |
| 2013/0218721 A1* | 8/2013 | Borhan | G06Q 20/322 | 705/26.41 |
| 2013/0284806 A1* | 10/2013 | Margalit | G06Q 30/06 | 235/382 |
| 2013/0297460 A1* | 11/2013 | Spivack | G06Q 30/0643 | 705/27.2 |
| 2014/0009378 A1* | 1/2014 | Chew | G06F 3/017 | 345/156 |
| 2014/0172610 A1* | 6/2014 | Carpenter | G06Q 20/40 | 705/26.1 |
| 2014/0211017 A1* | 7/2014 | Argue | H04N 7/18 | 348/150 |
| 2014/0214577 A1* | 7/2014 | Acker, Jr. | G07G 1/0081 | 705/23 |
| 2014/0236764 A1* | 8/2014 | Argue | G06Q 30/0613 | 705/26.41 |
| 2014/0279713 A1* | 9/2014 | Calman | G06Q 20/3224 | 705/418 |
| 2014/0282162 A1* | 9/2014 | Fein | G06F 3/0486 | 715/769 |
| 2015/0012396 A1* | 1/2015 | Puerini | G06Q 10/0875 | 705/28 |
| 2015/0019391 A1* | 1/2015 | Kumar | G07G 1/0036 | 705/28 |
| 2015/0178640 A1* | 6/2015 | Balakrishnan | G06Q 50/30 | 705/13 |

OTHER PUBLICATIONS

Anonymous, "Smart stores: Enhancing the retail customer's shopping experience", IBM Business Consulting Services, Dec. 2003. (Year: 2003).*

Dombusch, Jane, "Scan on a mission Stop & Shop's new smartphone app works as a super-fast self-checkout", Boston.com, Dated Nov. 9, 2011 (Year: 2011).*

Anonymous; "Shoprite Mobile Scan Use your smartphone to scan your groceries as you shop, then pay and g!", Shoprite.com , Circa 2012. (Year: 2012).*

* cited by examiner

METHOD AND SYSTEM FOR AUTOMATED RETAIL CHECKOUT USING CONTEXT RECOGNITION

CROSS-REFERENCE TO RELATED APPLICATIONS

This patent application claims the benefit of U.S. Provisional Patent Application Ser. No. 61/857,994, filed 24 Jul. 2013, the disclosure of which is incorporated herein by reference.

FIELD OF THE INVENTION

The present invention pertains to methods and systems for tracking human gestures, and particularly for methods and systems that enable retail purchases of goods using context recognition and gesture tracking.

BACKGROUND OF THE INVENTION

Many retail stores including shopping centers, grocery stores, clothing stores and others employ an age old method for receiving payments from customers who purchase products in the store. This method includes enabling the shopper to choose various goods to be purchased, place those goods in a shopping container, and providing a point of sale checkout mechanism such as a cash register or a self-serve payment system.

Modernly, products typically carry a product identifier such as a price tag, barcode, or radio frequency identification device that enables identification of the product and price of the product. During checkout a product identifier communicates with the checkout mechanism to tally the goods to be purchased, to calculate a purchase price and to enable payment.

For many years retailers have actively improved point of sale checkout systems to enable customers to more quickly and easily purchase goods. Improvements including barcode readers and radio frequency identification tag readers that enable the checkout process to be faster and easier. In this way there are less items that require a store employee to to physically read a price tag and type prices into a cash register.

Still there is room for improvement because customers are still required to queue in checkout lines and pass each product from the shopping cart or basket through a scanner. These customers are typically also required to swipe a credit or debit card during the checkout procedure. In other cases smart phones, or other electronics devices including smart cards having near field communication capability are used to complete transactions.

What is desired is a way of enabling customers to purchase goods in a retail store without having to queue for checkout. What is also desired are improved ways to manage inventories, and prevent theft.

SUMMARY OF THE INVENTION

The system of the present invention includes at least one sensor-equipped server mounted within a retail store to obtain an un-occluded perspective of a retail store floor. In one embodiment an array of sensor-equipped servers are capable of communication with each other and remote sensing devices situated across the retail floor.

Preferably the remote sensing devices maintain operative communication with the server(s) and are optimally positioned within the retail store to detect products (objects) and customer gestures. Positioning servers in a store minimizes system latency. Optimally the servers are attached to the ceiling of the retail store.

When a customer enters the retail store, their biometric features including facial characteristics, gait, retinal image, and other biometric indicia enable the sensor-equipped server to automatically identify the customer. One identified, the customer continually interacts with the server through explicit or implicit communication, or both, which are detected by the sensors and communicated to the server.

Additional Data available in electronic form can be used to improve the customer identification. Images, text, and streamed data such as audio and video associated with customers from publically available sources can be used to bolster the efficacy of customer identification. Such images, text, and streamed data may be sourced via social media web sites including Facebook™, Linkedin™, Google+™ and other web-based sources. Although these popular social media sources are listed, one can appreciate that the present invention may be integrated into any social media platform or source that could be developed in the future.

The system includes a financial database server, located locally or remotely to enable financial transactions. The financial database server communicates with the sensor-equipped server located in the retail store via a communications network such as the Internet.

The system also includes a biometric database server, located locally or remotely, or configured as part of the sensor-equipped server, to facilitate biometric identification. The biometric identity, verified by the sensor-equipped server, is mapped to a customer financial payment methods, such as a checking account, and communicated to the financial database to authenticate access to the shopper's preferred form of payment. The Additional Data described above is accessed and processed by the biometric database server to optimize the step of biometric identification. In an alternate embodiment, the sensor-equipped server processes the biometric information collected in the store and compares it to the data stored in the biometric database server.

Figure 1:
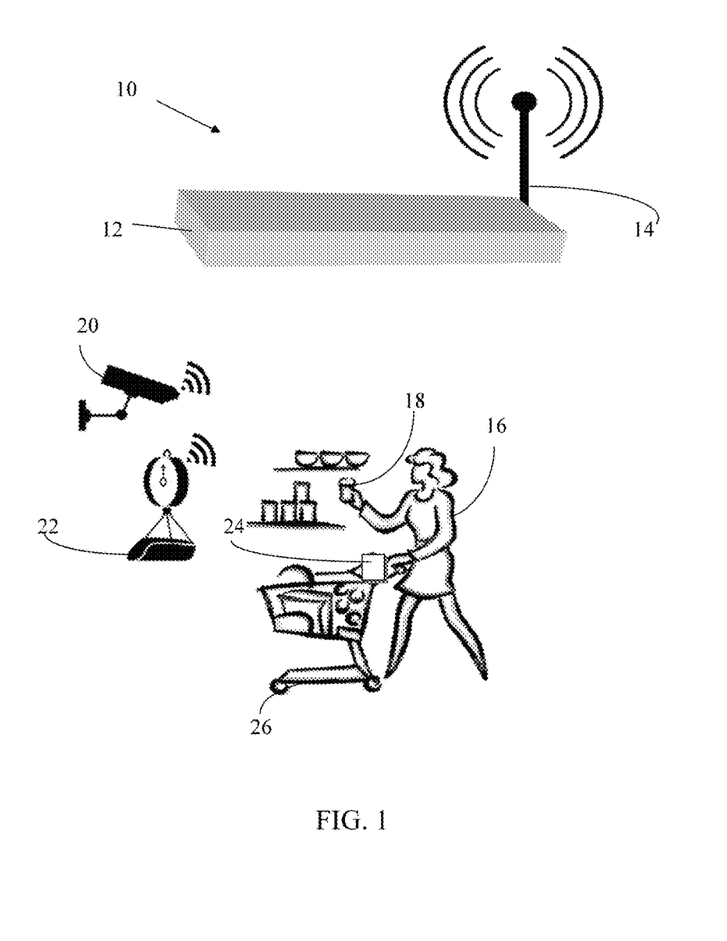
FIG. 1 is a shopper and components of the system of the present invention.

FIG. 1 shows a customer 1 performing various gestures that are recognized by the sensor-equipped server including: The Pick (P) gesture, which includes taking a object (i.e. product) from its shelf. The equivalent reverse gesture is: Return (R), in which a customer returns an object to a shelf.

The customer 1 transports a container such as a shopping cart through the retail store. The sensor-equipped server identifies the container transported by the customer. Although a shopping cart is shown in FIG. 1, the container can be any identifiable container such as a bag, basket, box, a clothing pocket, or even a hand of the customer.

Algorithms running on the sensor-equipped server identify gestures of the customer, including placing an item into the identified container. This is defined as a Commit-to-Container gesture, which is termed herein as a (C) gesture. C gestures cause the price/description associated with the committed item to be added to an electronic shopping cart.

In one embodiment, each C gesture is recorded in a continuous tally that is communicated to the customer via an electronic device attached to a shopping cart, or an electronic device carried by the customer. In another embodiment, a batch tally is provided at check out. Both tally types may be sequentially employed in conjunction with the present invention.

Preferably each C gesture is analyzed with three elements initiated by a customer. For example, the customer initiated steps of: 1. pick-up, 2. motion, and 3. drop. Pick-up is when a product is lifted from a location such as a shelf. Motion is identified when the picked-up product is moved. Drop is identified when the moved product is delivered to the container such as a shopping cart.

Products subject to a C gesture are particularly identified by the sensor-equipped server. In particular the identification is enabled for packaged goods by pattern recognition and location. Product location data is pre-recorded in a database so the likelihood of identification of any product is good when the shelf location is determined in view of the database. Also the size, color and shape of the product are identified visually and compared to the location data. The cooperation of visual data and location data yields a high probability of correctly identifying packaged goods. Text on a label of a packaged item and other indicia can also help improve certainty of goods subject to a C gesture. Further, bar codes and RFID tags affixed to packaged goods can communicate information in readable form by the sensor-equipped server.

Where the hand of a customer covers a packaged product label, the product can be identified by the sensor-equipped server when the product is moved i.e. dropped into a shopping cart or other container.

Regarding non-packaged foods such as produce, the product identification can be achieved by using location, product shape, size and estimate weight based on a volumetric calculation performed by the sensor-equipped server. Product bins can have sensors including weight and optical sensors to add certainty to product identification.

The server executes a Buy (B) function, when the customer gestures that the customer is ready to consummate a financial transaction. For example, the customer transporting any item or items that are represented in the electronic shopping cart, and physically located in the identified container, across a pre-determined region of the retail store causes the server to execute the Buy (B) function.

In an alternate embodiment of the invention the customer gesture selects an item on a shelf. The item remains on the shelf and the retail store adds the selected item to a container positioned in a fulfillment portion of the store. In this way the customer need not carry any items, and the fulfillment of the financial transaction occurs upon exit from the store, or later. In this embodiment, simply pointing to an item is an example of a gesture that can be identified by the sensor-equipped server. The need to deposit an item in a container is bypassed.

It can be appreciated that a combination of selecting items with a gesture and placing items in a container can be both used in the same retail store.

In one embodiment of the invention, the sensor-equipped server is rendered as a Geo-Context Panel (panel). Panels, suspended from the ceiling, spaced uniformly throughout the store, are connected in operative communication with each other. The panels collect and process sensor data in order to enable a gestural checkout using an electronic shopping cart associated with the shopper. The electronic shopping cart is a table within a database that stores prices, products identification and description data associated with customer's shopping choices. One benefit of using Geo-Context Panels is that modular installation of the system of the present invention is enabled without requiring modification of the store (except for minor ceiling modification). Another benefit is that the system is non-invasive from a customer viewpoint because ceilings are typically not within the constant purview of direct customer experience.

In one embodiment of the invention, each panel is rectangular in shape and the edges of each panel each contain 3D depth sensor mounted on a rotisserie which return a point cloud with x,y,z voxel (volumetric pixel or Volumetric Picture Element) position estimates for each point associated with an object's depth. The rotisserie allows the frustum of the depth sensor to be angled as needed to achieve aisle volume saturation. The 3D depth sensor itself can be based on infrared, ultrasound, EMF, stereo vision or other signaling modality capable of resolving 1 cm features at 3 meters, or better. In this way nearly all points within a retail store are detectable by the system of sensors that communicate with the with the network of panels.

The sensors include a system of cameras, preferably high definition cameras, positioned nearly concentric with the source of the 3D depth sensors and mounted on the same rotisserie. The panel includes lighting, preferably, LED lighting to illuminate the retail store. Supplemental lighting is also provided in the retail store, preferably on the ceiling. This yields optimal lighting for consistent image and video quality and product presentation. Output from the 3D depth sensor and camera are calibrated to a centimeter resolution, extended UTM based coordinate system for the store, allowing image pixels to be co-registered to 3D depth sensor voxels.

In one embodiment shoppers are provided with, or carry their own mobile electronic devices. Such mobile electronic devices may include mobile smart phones programmed with an appropriate software application. Each mobile electronic device communicates via Bluetooth, 802.11x or other wireless networking protocol. Such protocols include those in use, or to be developed.

The wirelessly networked mobile electronic devices enable communication between shoppers' mobile devices, the panel, and also with nearby 3D depth sensors, cameras or other remote sensors. The sensors allow for multiple perspectives to track movement of customers in the centimeter range. Mobile devices also enable another way to identify customers and track customer movement through a retail store via indoor localization methods. Analytical data regarding customer shopping patterns can be compiled and used by the retail store and others to maximize store design and presentation of products to customers.

Network Hardware

In one embodiment, communication between the panels is facilitated by a low power Server System in Chip (SSoC) which contains an embedded network fabric switch capable of interconnecting thousands of SSoCs. Similar to how cell phone users are switched between towers, as a shopper moves between panels, the mobile device carried by the shopper is automatically switched to the succeeding one. A digital object representing the shopper's state is maintained on the shopper's current panel, and her forward and backward panels. Excess compute capacity, far beyond what is required to support implicit gestural checkout, is resident in the panel unit to facilitate low latency mobile cloud computing.

The SSoC acts as master to a low power, smart phone class, multi-core SoC switch integrated FPGA, acting as slave. They are connected via Ethernet. 3D depth sensor, camera, microphone, and other sensors are directly connected to the smart phone class SSoC. The smart phone class SSoC serves as a sensor controller.

Either GPU, or a many core CPU Network on Chip (NoC), serves as a co-processor to the SSoC. Generally, sensor data collected by the smart phone class, SSoC is sent to the GPU/NoC to be de-noised and vectorized, and prepared for pattern recognition and machine learning.

A Neural Net ASIC (NNA) serves as a second co-processor to the SSoC. It is a highly parallel, scalable, neuron-based, vector pattern recognizer. The NNA receives de-noised vectors from the SSoC, processed earlier by the GPU/NoC.

Wireless Implicit Gestural Scales (IGS), HD Cameras and 3D depth sensors serve as peripherals to the panel, communicating sensor streams from partially occluded perspectives, such as within a refrigerator or under an overhanging shelf to capture unique points-of-view. For bulk items, shoppers' gestures and motion are tracked from the Pick event at the bin to the drop event at the IGS. The IGS contains a miniature 3D depth sensor, camera and a wireless radio, such as an 802.11x radio) allowing the product to be identified as it is being weighed. Both product identity and weight are sent to the panel, where the item total is tallied and added to the shopper's electronic cart.

Produce and Bulk Items

In one embodiment of the invention, sensors such as high definition cameras and 3D depth sensors observe the removal of product from bins. A database in communication with the panel's stores product data, including density. This database can be stored on one or more panel's or on a remote server in communication with the panel's. Accordingly, the volume of product removed from any bin by a customer is estimated, and based on that estimate a weight is calculated.

In yet another alternative embodiment, products are sold based on volume, or by the piece. This eliminates the need for weighing product and for enabling the various sensors of the present invention to make volumetric observations.

For example, in the produce section of a grocery store, the green peppers are sold by the piece, or by volume. The grocery store, having data reflective of the average weight or density of the green peppers, can set the price per-piece accordingly.

In yet another embodiment, scales are provided that communicate wirelessly, or via a wired connection, with the panel to automatically communicate weight of products to the panel. A scale can be located in the produce section of a grocery store, or incorporated into each product bin. In this way, when a product is removed from a bin or shelf, the product weight can be determined when the customer uses a scale in proximity to the bin or shelf. The panel calculates a price based on the weight and tallies this price with other items collected by the shopper, in the shopper's electronic cart.

Customer Biometric Identification

High Definition (HD) cameras with 3D sensors are placed at the entrance to the store collect image data including video and images data of the customer upon entry. This sensor system communicates data wirelessly with the nearest panel.

The panel is programmed to operate a face detection algorithm running on an SSoC on the panel. The algorithm, for example, isolates facial images in a bounding box using Viola-Jones or other object detection framework, and the pixilated data within the bounding box are sent to the GPU/NoC where the background is removed, key facial feature data is extracted and vectorized. The vectorized data is sent to the NNA, where it is compared to a database of registered shoppers for that store.

In one embodiment, the customer recognition data from the biometric server includes regional data, i.e. from the neighborhood surrounding the store location.

If a match is found, a variance is calculated between the stored (trained) facial representation of the shopper and the current one. If the variance is above a certain threshold, then the stored representation is updated to reflect the latest version of the shopper's face. In this way, especially in the case of supermarkets, where shoppers tend to shop weekly, facial representations can keep step with natural changes to a shopper's face due to weight gain or loss, facial hair, etc.

Voxel data from the 3D sensors, front facing remote cameras and overhead cameras within the panel is co-registered (fused), allowing a correspondence to be made between the pixels representing the face of the shopper and the pixels representing the top/back/side of the shopper's head (overhead view). This allows the shopper to be tracked as they move about the store by the front/top/back/side of their head by the panel.

A voxel is a volume element, representing a value on a regular grid in three dimensional space. This is analogous to a pixel, which represents 2D image data in a bitmap (which is sometimes referred to as a pix map). As with pixels in a bitmap, voxels themselves do not typically have their position (their coordinates) explicitly encoded along with their values. Instead, the position of a voxel is inferred based upon its position relative to other voxels (i.e., its position in the data structure that makes up a single volumetric image). In contrast to pixels and voxels, points and polygons are often explicitly represented by the coordinates of their vertices. A direct consequence of this difference is that polygons are able to efficiently represent simple 3D structures with lots of empty or homogeneously filled space, while voxels are good at representing regularly sampled spaces that are non-homogeneously filled.

Training for Implicit Gestural Checkout

Automatic Recognition of sources in 4 categories: a) Manufactured Objects (M) of fixed geometry, i.e., a can of soup, b) Grown Objects (G) of variable geometry, i.e, an apple, c) physical gestures (P) (which would include gait, height, volume, etc.) and d) Faces (F) are facilitated through a subsystem that captures essential features of the sources and stores these features as patterns for subsequent pattern matching (recognition).

Data specific to M which provides image, geometry and product description can often be obtained from commercial databases. Image data of F can also be obtained from databases, or acquired directly from shoppers at registration-time via camera. However, for G, P and M, in the case where no database exists, image and geometry acquisition will be acquired using an 3D Implicit Scanner (3DIS), an apparatus consisting of computer, HD camera and 3D sensors enclosing a cubic volume, and providing 360 degree coverage of any object placed within the enclosure. An operator controlling the 3DIS, places an prototypical specimen of the object within the enclosure, keys an object description, and initiates image and 3D capture of the object geometry. For G or M, a single capture frame is sufficient. For P, when the object is a subject demonstrating a gesture, multiple capture frames per second can be acquired over a duration to completely define the gesture.

Geometric output from the 3DIS is rendered in the form of a point cloud. Output from either commercial databases or 3DIS is converted using 3D modeling software into a mesh model and rendered using images for texture, where appropriate.

The topology of the mesh model is then morphed (generalized and optimized) using morphing software to produce m variations of the original, prototypical source. In the case of G, this amounts to variation, deformation in the shape, size, color, etc. of the grown object. In the case of P, this amounts to variation in height, weight, body type; moving through the spectrum of endomorph, mesomorph, ectomorph. F is a special case, requiring morphing of expression, profile, facial hair, shades, weight gain/loss, etc. M has no topological variation, and does not pass through this stage.

The m topological variations of the original prototypical object of gesture are then animated within a gaming engine, where the gaming engine's virtual camera is used to capture multiple Points-of-View (POV) from various x,y,z locations around the object. These POVs correspond to the perspectives taken from the panel, IGS, and other wireless sensors. For every m topological variation, n POV variations are acquired, resulting in an m×n variation matrix.

Each element of the m×n variation matrix is de-noised, normalized to scale and vectorized. Vectorization, extracting the essential characteristic of M, G, P, F, will employ algorithms specific to each type. In the case of M and G, where texture (appearance) is key to identification, appropriate computer vision algorithms will be applied to represent image, color, text, as required. For P, algorithms focused on the human skeleton, specifically the angles made by the joints, will be employed for vectorization. For F, algorithms leveraging eye width, nose to chin ratios, etc. are used.

The vectors (patterns) will be stored on Random Mass Storage (RMS) device where they can be read directly by a parallel Cognitive Processor (CP), or equivalent, allowing for the simultaneous comparison of a given input vector to thousands of other stored vectors to affect a real-time match.

In the case of P, a level of tailoring and personalization can be achieved by treating the retail space itself like a large 3DIS. A gesture used to pick from a horizontal, waist high produce bin is different from a gesture used to pick from a high vertical shelf (Note: the panels over the horizontal bins in produce would run gesture patterns appropriate to that context. panels along the refrigerated aisle would run gesture patterns appropriate to that context, etc.) Someone who is using a wheel chair may pick using a tool. Once identified, the system can train on an individual's picking style, as it would any other, and recall that pattern from RMS when the individual is in the store to help reduce error rate and improve authentication.

Implicit gestural checkout eliminates the need for scanning product barcodes. Product identity is associated with the product appearance, geometry and location.

Shoppers need not carry cash, debit or credit cards in order to make a purchase. Shopper authentication is driven by the shopper's biometrics. Once authenticated, and the transaction is committed, the shopper's checking account is electronically debited, directly.

Suspected IMPLICIT GESTURAL THEFT (IGT) is detectable as a corollary of IMPLICIT GESTURAL CHECKOUT; defined as an occurrence of product-pick without the occurrence of offsetting product return-to-shelf, or product-commit-to-known-container actions by a registered user. When a theft context is detected, excerpted video is sent to security persons for final evaluation.

A smart-phone is not required. The current state of the shopper's electronic cart can be obtained, confidentially, by standing in front of a display, such as a tablet display. The tablet display may be one of many distributed throughout the store. Alternately, the state of the shopper's electronic cart can be transmitted to their mobile device via 802.11x.

Accordingly, in one embodiment of the invention, the customer's smart phone includes an application stored on the smart phone to enable the smart phone to communicate directly with the panel to receive electronic shopping cart data including products selected and associated prices as well as subtotals. The application causes the phone to alert the customer when a product is added to the shopping cart. The alert generated by the phone can be an illuminated indicator, such as a light emitting diode (LED). The alert can also include a vibration, an image or video, or a sound.

Upon receipt of the phone signal indicating that a product has been recognized by the Implicit Gestural Checkout system, and added to the electronic shopping cart, the phone offers the customer an option to reject the item from the electronic shopping cart by returning to the product to the shelf.

Importantly, because the items selected by a customer may be characterized by more data than appears on the label, the app may be enabled with a toggle to provide more detailed item information to the customer. The more detailed data can include nutritional information, allergy warnings, or any subset of data desired by the customer. The application is configurable by the customer to enable the customer to selectively filter the more detailed data.

For example, the application can be configured to provide the customer amino-acid profiles directly to the customer upon actuation of the toggle. Another example enables the application to be configured to provide ratios of omega-3 fatty acids to omega-6 fatty acids contained in the item. A further example is to provide the customer with data related to allergens that the customer has pre-programmed the application to filter.

In an alternate embodiment, the application contains data describing the origin of each ingredient of the item. For example, a packaged product may contain ingredients sourced from Brazil, and other ingredients sourced from California. Such information can be provided to the customer. Further, specific details describing the manner of production, i.e. organic, fair trade and other certifications can be indicated to the customer by the application running on the smart phone.

Although the use of a smart phone and applications running on the smart phone, it is anticipated that other mobile devices may be used to communicate product data to a customer, including wearable technology such as Google Glass™ technology sold by Google, Inc.

Capture Object Context

Geo Context Panels (panels), consisting of cloud computer, mass storage, camera, 3D depth sensor, speaker, microphone, wireless and wired networking are installed, suspended from the ceiling on alternating sides and separated according to the limits of the range of their 3D sensors. Each panel is simultaneously a super node on a fiber connected, hybrid IPV4/IPV6 network and acts as an 802.11x access point.

An initializing panel is given its absolute UTM x (northing), y (easting), z (vertical) position coordinates by an operator. It communicates its position to its nearest panel peer. Using 3D sensing, and distance approximation algorithms, the panels calibrate the position of its nearest peer. This process cascades across all units in the Geo Context Panel Plex (panelP, all the panels in the installation)

After all panels are initialized with their exact positions, from within a fully inventoried, but otherwise empty (of people and extraneous objects) space, they 3D scan and image their immediate vicinity (limit of 3D sensing range). A 3D model from their ceiling perspective is constructed. Individual models from each panel are stitched together to form a corse-grained, comprehensive 3D model of the entire space (store). The corse-grained comprehensive model is stored in a GeoSpatial database and distributed across all panels in the space.

Geo Context Copters (GCC), equipped with 3D sensor, camera, microphone and autonomous flight capabilities, communicate wirelessly to the panels using 802.11x. Sinusoidal flight paths, based on the contours of the objects within the coarse-grained geometry earlier constructed by the panels, are computed and transmitted to the panel. Centimeter accurate x,y,z localization (determining position) of the GCC in flight can be done by means of ultrasound or other signaling modality. In one embodiment, the panels emit 4 bands of ultrasound that are recorded by the GCC, and sent back to the panel for cross correlation to determine absolute distance from the panel's signal sources.

Audio, video and 3D sensor data are streamed back to the nearest panels from the GCC. The panel determines the GCC's current position. Simultaneous Localization and Mapping (SLAM) or similar algorithm to is used to compute a fine-grained, comprehensive 3D model of the space. Repetitive Structure Detection algorithms are run against the image data acquired by the GCC to isolate unique objects in the image stream.

Object detection, based on Viola-Jones or similar algorithms, running against an object database, and computer vision image recognition are augmented by crowd-sourced, human object detection and recognition to categorize objects, and associate them with both i) common name and ii) unique industry standard Universal Product Code (UPC) or other unique identifiers. In the case where an organization has a planogram, and/or organization specific object identifiers, that data will be integrated into an object's data representation.

Curated content sourced from host organizations or third parties, is integrated with directed object directed search content from the www to form a corpus. Text and images from the corpus are indexed. Curated apps and object-relevant apps discovered in App stores apps are installed in open sourced OS/mobile device specific Virtual Machines (VMs).

Hierarchical clustering, or similar algorithms, run against the corpus are combined with existing sources like the Wikipedia Producer Ontology and crowd-sourced micro-tasking to create and align object ontologies semi-automatically. Object ontologies, consisting of object description, properties, relationship to other objects, etc. are stored in an Ontolological database.

The objects are indexed with respect to their x,y,z location, UPC or other unique, standard identifiers within a GeoSpatial database and cross linked to their, respective, ontologies in the Ontology database.

Changes to the position of existing objects, or the introduction of new objects in to the panelP can be mediated directly by the panel, GCC or manually using a smartphone equipped with a localizing Geo Context Application (GCA) capable of communicating with the panel.

Smart Phone Application

An application programmed on a user device having a processor and a user interface including a display and a speaker. The application includes software controlled by the processor that performs the steps of: enabling communication between the user device and a server; providing sensors in operative communication with the server, the sensors being in proximity to the user device to enable recognition of a user, and gestures of the user; recognizing a gesture with the sensors and the server indicating a customer choice to purchase a product and add the product to an electronic shopping cart; and communicating the choice to the customer user device.

Various embodiments of the invention include those having the user device enable the customer to selectively reject the choice, which assures that mistaken charges will not appear on the electronic shopping cart.

The user device enables the customer to gather personalized product data such as data describing coupons relating to the items purchased, a tally of the shopping cart items, descriptions of nutritional content of the items, health benefits and drawbacks of the items, and other information that would enable the customer to make an informed buying decision.

The server detects a gesture indicating an intention to check out, and automatically consummates a purchase transaction for the items in the electronic shopping cart.

The server detects a gesture indicating an intention to check out including movement of the customer within a pre-defined geography, and automatically consummates a purchase transaction for the items in the electronic shopping cart.

In another embodiment, the server detects a gesture indicating an intention to check out including movement of the customer within a pre-defined geography, such as a retail store exit, and automatically consummates a purchase transaction for the items in the electronic shopping cart.

DETAILED DESCRIPTION

FIG. 1 shows a system generally designated with the reference numeral 10. The system includes a sensor equipped server including a geo-context panel 12 with a wireless antenna 12. The panel 12 communicates with numerous sensors 20 positioned within a store location and with numerous devices 22. The sensors 20 and the devices 22 are enabled to identify products within a store location. The device 22, as shown, includes a scale for weighing produce. The device 20 includes a wireless antenna and control circuitry for communicating with the panel 12. The device 22 is equipped with video capability, control circuitry and a wireless antenna for communicating with the panel 12.

A shopper 16 is shown selecting an item 18 and removing the item 18 from a shelf and depositing it into a container 26.

The container 26 is a shopping cart, as shown. However it can be appreciated that the container 26 may also be a basket, bag, a pocket of a customer, or any mechanism for holding items 18.

An electronic device 24 provides the customer with a display capable of displaying a list of items selected and placed in the container or cart 26. This list includes price information and may be programmed to provide detailed product information, or even information about competing products.

In one embodiment, on-line adds for similar products and bulk pricing from on-line sources are provided to the customer via the electronic device 24.

In one embodiment, the electronic device 24 is programmed to detail product information including rating products based on a customer's preferences, or health goals. In addition the electronic device 24 is programmed to be able to display detailed nutrition facts relating to the item, including information not found on the label.

In one embodiment, the electronic device 24 is attached to the cart 26, or to a shopping basket, and maintain electronic communication with the geo context panel 12. This enables the exact location of the shopper and the electronic device 24 to within centimeter accuracy, which facilitates item identification by the server to be rapid, and nearly error-free.

The electronic device 24 may also include an RFID reader, bar code reader, or optical sensors to further facilitate product identification and confirmation of purchase decisions by the customer 16.

In another embodiment, the electronic device 24 is a smart phone, tablet or other computing device carried or worn by the shopper, or attachable to the cart 26. The electronic device 24 is programmed with appropriate applications to facilitate shopping, executing various steps in accordance with the present invention, and for interacting with the systems of the present invention.

The scale 22 The scale 22 enables the shopper 12 weigh produce items. The scale 22 is equipped with wireless communication hardware to automatically communicate the weight and item description to the panel 12. The video camera 2b is positioned in proximity to items on shelves and the shipper 16. The video camera 20 includes wireless communication hardware and automatically observes movement of the shopper 16 and communicates the shopper's movement, including gestures, to the geo-context panel 12.

Figure 2:
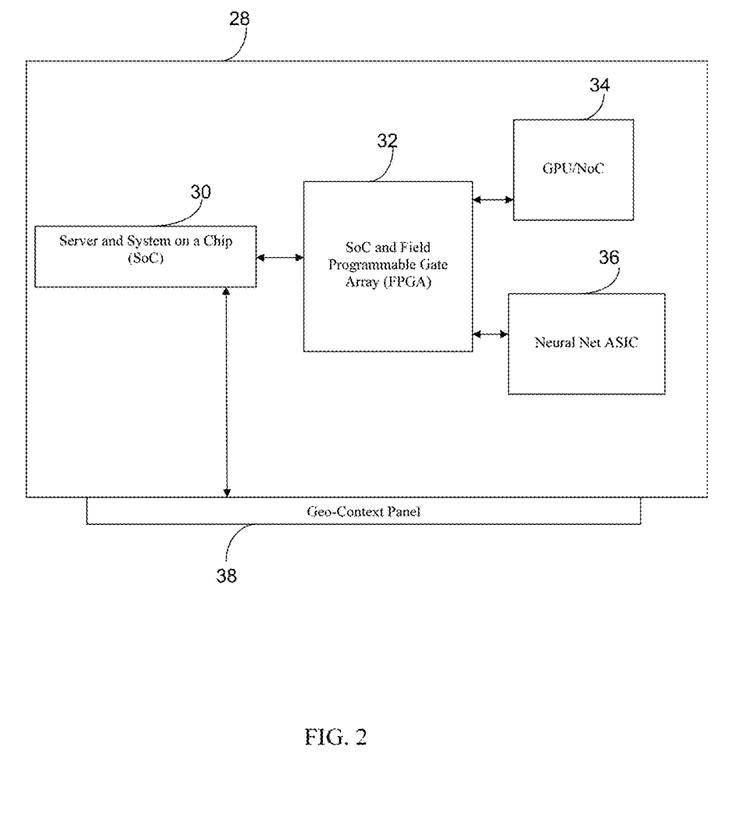
FIG. 2 is a system diagram of a geo context panel and computer in accordance with the present invention.

FIG. 2 shows a system 28 including a geo-context panel 38 integrated with a server 30, a system on a chip (SOC) and field programmable gate array (FPGA) 32, a GPU/NoC 34, and a neural net ASIC 36, all in operative communication and co-located with the panel 38. GPU is a general processing unit, and the NoC is a network on a chip configuration.

The FGPA 32 is an integrated circuit designed to be configured after manufacturing—hence "field-programmable". The FPGA configuration is generally specified using a hardware description language (HDL), similar to that used for an application-specific integrated circuit (ASIC). The FGPA is in operative communication with the GPU 34 and a Neural Net ASIC 36. The server 30 includes appropriate hardware and software to enable observation through the panel 38 of movement and identification of shoppers and items within a store. The server 30 is also enabled with appropriate hardware and software to enable communication with remote data sources via a network to facilitate confirmation of shopper identity and the identity of items.

Figure 3:
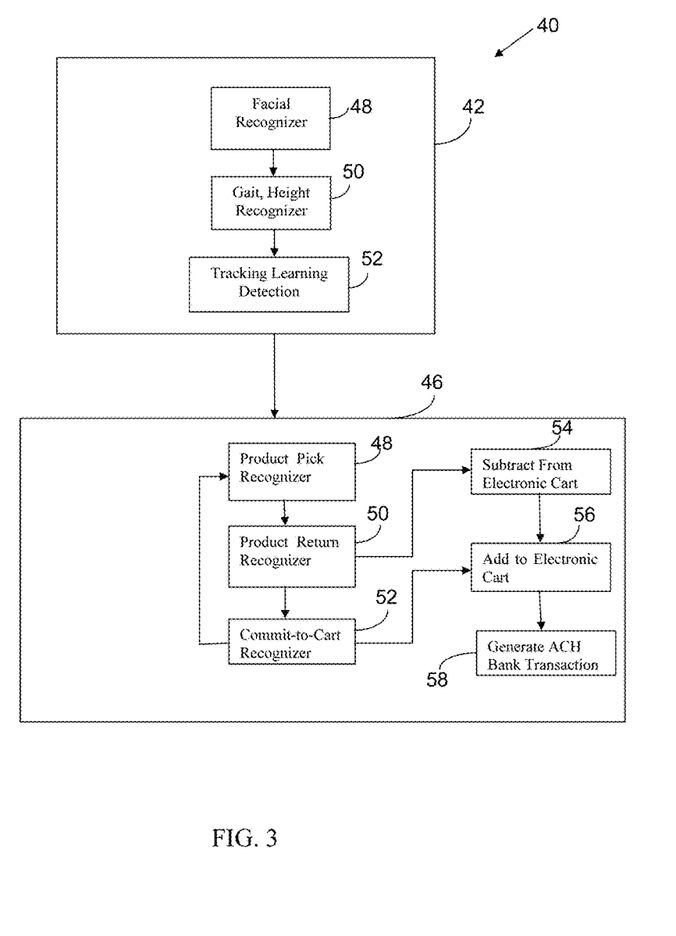
FIG. 3 is a flowchart of a method of identifying a customer and providing an implicit gestural checkout in accordance with the present invention.

FIG. 3 shows a system generally designated with the reference numeral 40. The system 40 includes a shopper identity verification module 42 and an item identity verification module 46, both operated by the server 30 (FIG. 2).

The shopper identity verification module 42 is integrated with the server 30 and includes facial recognizer 48, a gait and height recognizer 50 and a tracking learning detection module 52. The facial recognizer 48 employs optical data, communication with stored data and remote databases, and appropriate algorithms to recognize shoppers. The gait and height recognizer 50 gathers and stores data, and associates the stored data associated with particular shoppers. Data characteristic of gait and other movement traits are stored along with biometric data of the particular shopper. Biometric data can include retinal scan data, height, physical dimensions and ratios of such dimensions.

The item verification module 46 is integrated with the server 30. Items such as packaged products, produce, and even service products should be included in the definition of "item" as used herein. The module 46 includes a product pick recognizer 48, a product return recognizer 50, and a commit-to-cart recognizer 52. Together the item verification module 46 detects when a product is selected, moved, and placed in a container such as a cart, bag, pocket or even contained in the hand of a shopper.

The product pick recognizer 48 identifies the item (i.e. product) selected by the shopper by shape, color, size and location within a store. Other indicia include bar codes, text and other label indicia. Further any product can be tagged with a radio frequency identification tag, or other similarly functional technology to enable product identification.

The return recognizer 50 detects movement of an item out of the container (i.e. cart) and back to any shelf or other location in a store.

Each time the product pick recognizer 48 recognizes a item has been picked and the commit-to-cart recognizer recognizes the intent to purchase the item, then the module 46 tallies the intent to purchase the item in an electronic shopping cart operated by the server. Items recognizes by the product return recognizer that have been previously tallied are subtracted from the electronic shopping cart.

The module 46, thus performs the steps of 56 adding an item to an electronic shopping cart, the step 54 of subtracting the item from the electronic shopping cart when a product return action is recognized, and lastly the step 58 of generating a bank transaction when a shopper leaves the store, or other pre-defined event. Preferably the bank transaction is an ACH transaction.

A method of object and gesture recognition training includes representing the source (a person or item) in three dimensions followed by electronically modeling or providing variants of the sources, next the method includes extracting essential patterns, and reiterating until authentication is achieved. The essential patterns are stored in random and mass storage. The random and mass storage includes a pattern matching algorithm and processing component.

The module 46 relies on a method of processing data including mapping 3-D geometry of a store, shelves and items on those shelves. Communicating with a remote database via the server enables item recognition and authentication of item recognition.

Figure 4:
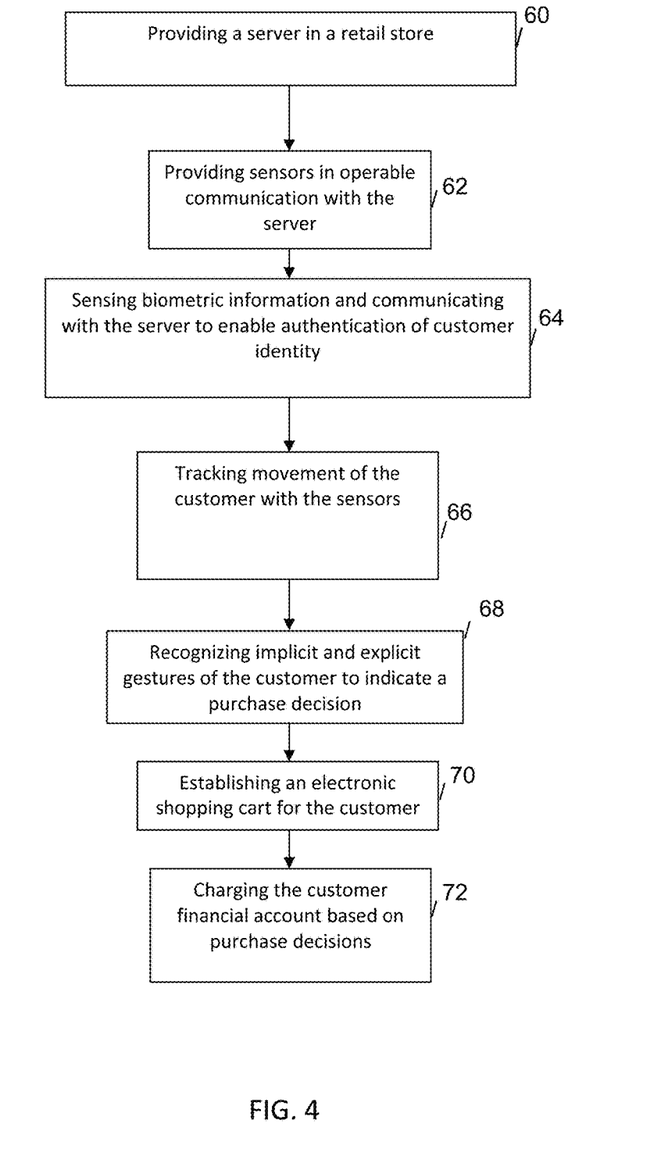
FIG. 4 is a flowchart of a method in accordance with the present invention.

FIG. 4 is a method including the step 60 of providing server in a retail store, the step 62 of providing sensors in operable communication with the server 62, the step 64 of sensing biometric information and communicating with the server to enable authentication of customer identity, the step 66 of tracking movement of the customer with the sensors, the step 68 of recognizing implicit and explicit gestures of the customer to indicate a purchase decision, the step 70 of establishing an electronic shopping cart for the customer, and the step 72 of charging the customer financial account based on the recognized purchase decisions.

FIG. 4 shows a method including the step 40 of providing a server in a retail store, the step 42 of providing sensors in operable communication with the server, the step 44 sensing biometric information and communicating with the server to enable authentication of customer identity, the step 46 of tracking movement of the customer with the sensors, the step 48 recognizing implicit and explicit gestures of the customer to indicate a purchase decision, the step 50 establishing electronic shopping cart for the customer, and the step 52 of charging the customer financial account based on purchase decisions.

Figure 5:
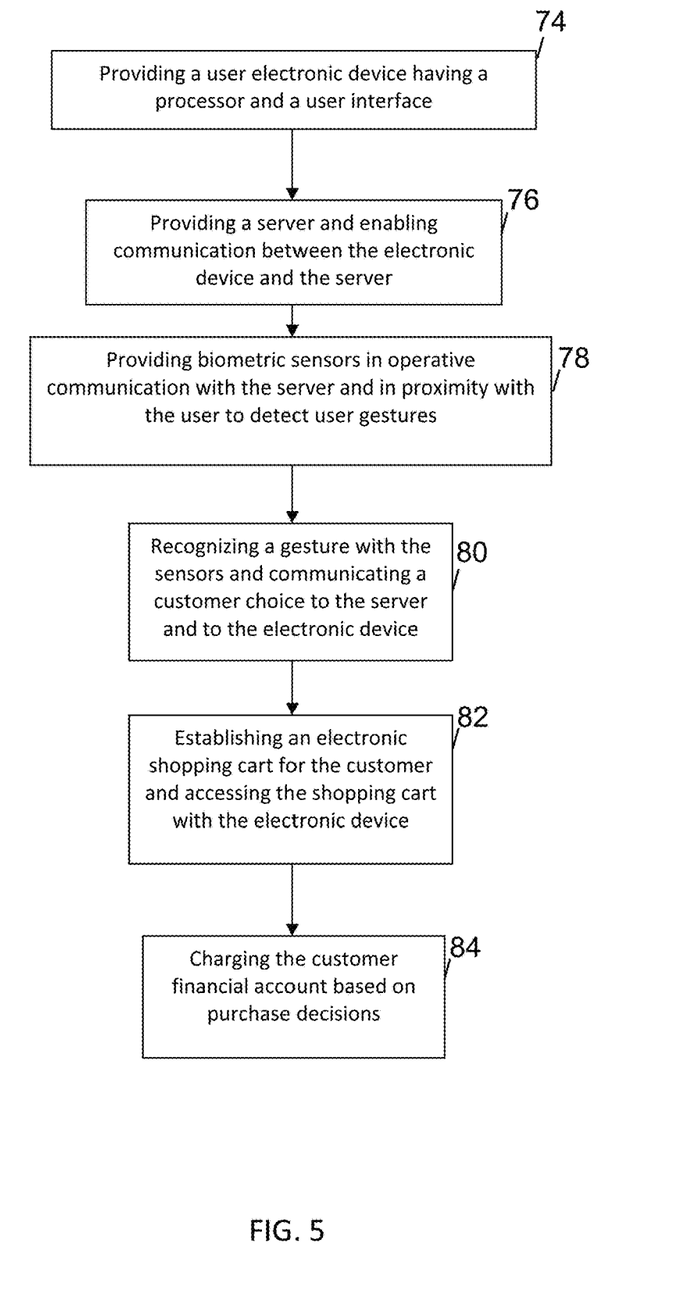
FIG. 5 is a flowchart of a method in accordance with the present invention.

FIG. 5 shows the step 74 of providing a user electronic device having a processor and a user interface, the step 76 of providing a server and enabling communication between electronic device and the server, the step 78 providing biometric sensors in operative communication with the server and in proximity with the user to detect user gestures, the step 80 of recognizing a gesture with the sensors and communicating a customer choice to the server and to the electronic device, the step 82 establishing electronic shopping cart for the customer and accessing the shopping cart with the electronic device, and the step 84 of charging the customer financial account based on purchase decisions.

Checkout is enabled when the customer passes through the demarcation zone with products selected by gesture.

Figure 6:
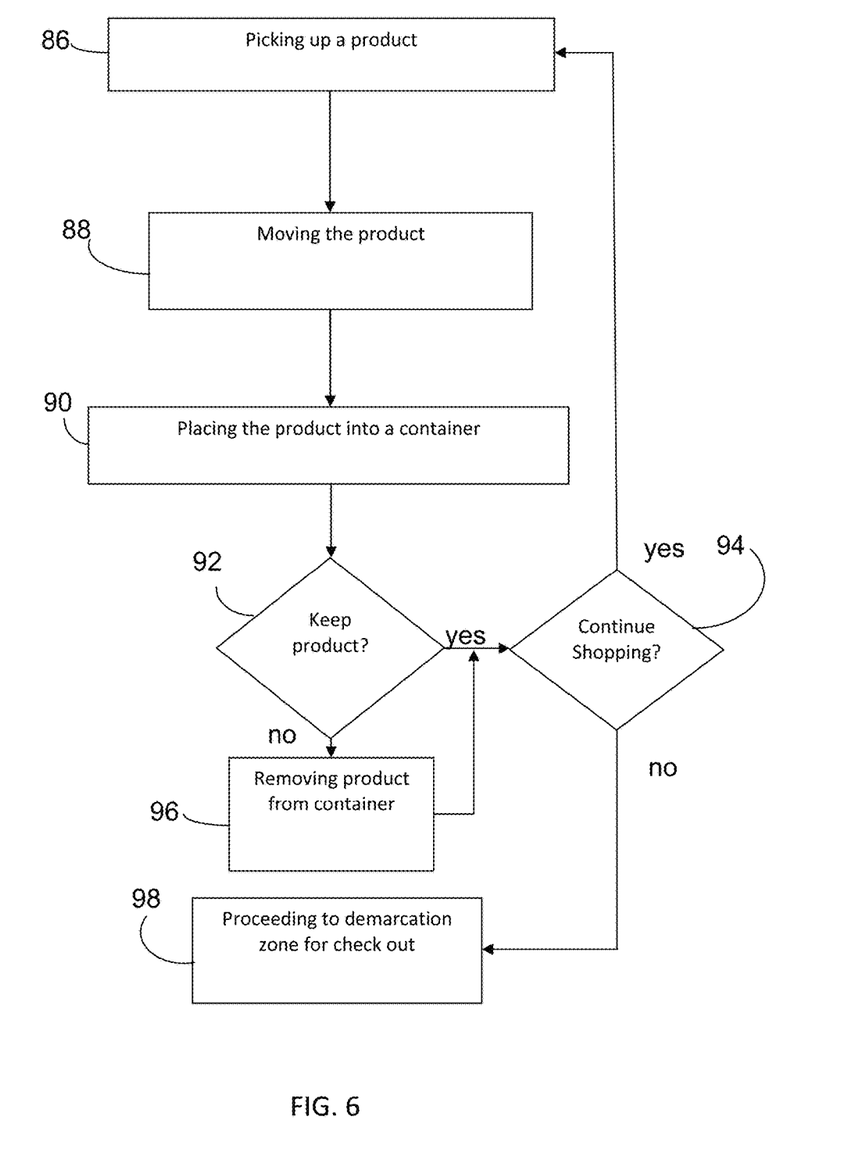
FIG. 6 is a flowchart of a method in accordance with the present invention.

FIG. 6 shows the step 86 of picking up a product, the step 88 of moving the product, the step 90 of placing the product into a container, the step 92 of deciding whether or not to keep the product, the step 94 of deciding whether or not to continue shopping, the step 96 of removing the product from the container, and the step 98 of proceeding to the demarcation zone for check out.

The step 86 of picking up a product consists of a customer reaching for a product, grasping the product from a shelf and lifting the product from the shelf. The customer being a person whose identity has been biometrically confirmed, or that customer's assistant. The sensor equipped server detects step 86 and all steps relating to FIG. 6. The shelf may be a physical shelf, or may be the floor, a refrigerator or freezer, or other way of supporting the product in view of the customer.

The step 88 of moving the product includes enabling the sensor equipped server to detect the customer grasping the product for a period ranging from a microsecond to a few seconds. Further, after the step 86 of picking up the product, the product is translated to the cart or other container.

The step 90 of placing the product into a container includes releasing the grasp of the customer on the product. The product may be placed by hand or by gravity into the cart or other container. The sensor equipped server is enabled to detect this step 90.

The step 92 includes the customer deciding whether or not to keep the product and the step 94 enables the customer to decide whether to continue shopping or not. In deciding whether to keep the product or not, if the customer performs the step 96 of removing the product from the cart or other container, then this movement is an indication to the sensor equipped server that the product is not being kept.

The step 94 enables the process beginning with step 86 to repeat until the customer decides to discontinue shopping in step 94. Next, the step 98 includes the customer proceeding to the demarcation zone for check out. The sensor equipped server senses the customer movement through the demarcation zone to batch tally the products moved with the customer.

The system can be adapted to detect theft based on gesture recognition. In one embodiment, the server is programmed with software to detect probable theft events, and the server reports probable theft events upon detection to store security personnel for verification. A theft event includes where a customer gestures to conceal an item and the system detects such concealment.

While the present invention is described in terms of various embodiments, having interchangeable features, these embodiments are by way of example only. The true scope and nature of the present invention is set forth in the appended claims.

The invention claimed is:

1. A method for enabling a customer having an identity to purchase goods from a retail store through the use of implicit gestures and a customer financial account, comprising:
  providing a server in communication with the retail store, the retail store including a demarcation zone, for enabling check-out, wherein the server includes one or more processors, computer memory with software, the software being programmed for enabling operation of the server to communicate with a plurality of sensors;
  providing a first and second plurality of sensors, in operable communication with the server, wherein the first plurality of sensors are optical sensors, and the second plurality of sensors are different from the first plurality of sensors;
  sensing biometric information of the customer with the first plurality of sensors and converting at least some of the biometric information into topological variations, communicating the biometric information to the server to enable the server to authenticate customer identity;
  tracking movement of the customer within the retail store with the second plurality of sensors;
  recognizing gestures indicating a purchase decision;
  tracking the purchase decision in an electronic shopping cart;
  the topological variations are then animated within a gaming engine having a virtual camera, where the gaming engine's virtual camera is used to capture multiple points-of-view from various locations around the customer, these points of view correspond to the perspectives taken from the first plurality of sensors; and
  enabling a checkout procedure when the customer is passing the demarcation zone by charging the customer financial account based on the purchase decision.

2. A method as set forth in claim 1, wherein the demarcation zone is positioned adjacent a store exit.

3. A method as set forth in claim 1, wherein the first plurality of sensors include optical sensors enable facial recognition and the server is programmed with facial recognition software to authenticate customer identity.

4. A method as set forth in claim 1, wherein the first plurality of sensors enable gait recognition and facial recognition, and the server is programmed with gait and facial recognition software to authenticate customer identity.

5. A method as set forth in claim 1, wherein the second plurality of sensors include acoustic sensors to track movement of the customer within the retail store and to recognize purchase decisions.

6. A method as set forth in claim 1, wherein each of the plurality of sensors communicate wirelessly with the server and are positioned in an array within the retail store.

7. A method as set forth in claim 1, wherein the customer has a hand, and the store has products placed on shelves, the step of recognizing implicit gestures includes optically recognizing movement of the hand to move a product from the shelf.

8. A method as set forth in claim 7, wherein the retail store provides shopping carts or the shopper brings their own shopping container, the step of recognizing implicit gestures includes 3D depth sensor/video recognition of movement of the product into a shopping container.

9. A method as set forth in claim 7, wherein the plurality of sensors detect the moved product to identify the product, the sensors communicate with the server to enable the server to determine a product price, the product price is recorded by the server.

10. A method as set forth in claim 9, wherein the first plurality of sensors detect multiple products moved by the customer to tally product prices and charge the customer financial account.

11. A system for enabling a customer having an identity to purchase goods from a retail store through the use of implicit gestures, a portable electronic device, and a customer financial account, comprising:
a server located within the retail store, wherein the server includes one or more processors, computer memory with software, the software being programmed for enabling operation of the server to communicate with a plurality of sensors;
a portable electronic device in operable communication with the server to allow a customer to accept or reject a purchase decision;
a first and second plurality of sensors in operable communication with the server for sensing customer biometric information and communicating the customer biometric information to the server to authenticate customer identity, and to associate the customer identity with a customer financial account;
the first and second plurality of sensors enable tracking movement within the retail store and recognizing gestures of the customer indicating a purchase decision;
the first and second plurality of sensors track the purchase decision indicated by a customer gesture, the customer gesture including picking up a product, moving the product and placing the product in a container, at least one of the first and second plurality of sensors detect topological variations in the product;
the topological variations are then animated within a gaming engine having a virtual camera, where the gaming engine's virtual camera is used to capture multiple points-of-view from various locations around the product, these points of view correspond to the perspectives taken from the at least one of the first and second plurality of sensors, and
the server enables a checkout procedure when the customer is detected by the third plurality of sensors as placing the product in the container by communicating the purchase decision to the portable electronic device for customer approval.

12. The system set forth in claim 11, wherein the retail store has an exit with a demarcation zone, the step of communicating the purchase decision and charging the customer financial account is initiated upon movement of the customer in the demarcation zone.

13. The system set forth in claim 11, wherein the first plurality of sensors include optical sensors having facial recognition capability and the server is programmed with facial recognition software to authenticate customer identity.

14. The system set forth in claim 11, wherein the server tracks the purchase decision when the customer removes a product from a shelf and places the product into a container;
the server communicates the purchase decision to the portable electronic device, and
the step of communication enables the customer to display information pertaining to the product with the portable electronic device.

15. The system set forth in claim 11, wherein the server also tracks the purchase decision if the customer removes the product from the container and re-places the product on to the shelf.

16. The system set forth in claim 11, wherein the server tracks the purchase decision when the customer places the product into a pocket of the customer.

17. The system set forth in claim 11, wherein the server tracks the purchase decision when the customer carries the product by hand through a demarcation zone defined within the retail store.

18. The system set forth in claim 11, wherein the server associates financial data with the customer, and charges the financial account when the customer passes a demarcation zone defined within the retail store.

19. The system set forth in claim 11, wherein the server associates financial data with the customer, and charges the financial account when the customer exits the retail store.

20. The system set forth in claim 11, wherein the server associates financial data with the customer, and charges the financial account after the customer exits the retail store.

21. The system set forth in claim 11, wherein the server is programmed with software to detect probably theft events, and the server reports probable theft events upon detection to store security personnel for verification, wherein a theft event includes where a customer gestures to conceal an item.

* * * * *